(12) United States Patent
Cox (10) Patent No.: US 6,540,774 B1
(45) Date of Patent: *Apr. 1, 2003

(54) STENT DESIGN WITH END RINGS HAVING ENHANCED STRENGTH AND RADIOPACITY

(75) Inventor: Daniel L. Cox, Palo Alto, CA (US)

(73) Assignee: Advanced Cardiovascular Systems, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/387,150

(22) Filed: Aug. 31, 1999

(51) Int. Cl.[7] .................................................. A61F 2/06
(52) U.S. Cl. ....................................................... x 623/1.15
(58) Field of Search ............................... 623/1.16, 1.15, 623/1.18, 1.19, 1.2, 1.34; 606/198

(56) References Cited

U.S. PATENT DOCUMENTS

| | | | |
|---|---|---|---|
| 3,105,492 A | 10/1963 | Jeckel | |
| 3,657,744 A | 4/1972 | Ersek | |
| 3,993,078 A | 11/1976 | Bergentz et al. | |
| 4,130,904 A | 12/1978 | Whalen | |
| 4,140,126 A | 2/1979 | Choudhury | |
| 4,159,719 A | 7/1979 | Haerr | |
| 4,241,146 A | 12/1980 | Sivachenko et al. | |
| 4,387,952 A | 6/1983 | Slusher | |
| 4,503,569 A | 3/1985 | Dotter | |
| 4,504,354 A | 3/1985 | George et al. | |
| 4,512,338 A | 4/1985 | Balko et al. | |
| 4,531,933 A | 7/1985 | Norton et al. | |

(List continued on next page.)

FOREIGN PATENT DOCUMENTS

| | | |
|---|---|---|
| DE | 195 37 872 A1 | 4/1997 |
| EP | 0045627 | 2/1982 |
| EP | 0062300 A2 | 10/1982 |
| EP | 0 201 466 A2 | 11/1986 |

(List continued on next page.)

OTHER PUBLICATIONS

Charnsangavej, Chuslip, M.D., et al., Stenosis of the Vena Cava: Preliminary Assessment of Treatment With Expandable Metallic Stents, *Radiology*, pp. 295–298, vol. 161, Nov. 1986.

Rösch, Josef, M.D., et al., Experimental Intrahepatic Portacaval Anastomosis: Use of Expandable Gianturco Stents, *Radiology*, pp. 481–485, vol. 162, No. 1987.

(List continued on next page.)

*Primary Examiner*—Michael H. Thaler
(74) *Attorney, Agent, or Firm*—Fulwider Patton Lee & Utecht, LLP (57) ABSTRACT

An expandable stent having end rings with enhanced strength and radiopacity for implantation in a body lumen, such as an artery, is disclosed. The stent consists of a plurality of radially expandable cylindrical elements generally aligned on a common longitudinal stent axis and interconnected by one or more interconnecting members placed so that the stent is flexible in the longitudinal direction. The expandable cylindrical elements have regions which are subject to high stresses and regions subject to low stresses when the cylindrical elements are radially expanded. In order to increase the radiopacity of the stent, the width of the strut in the low stress region of the stent is designed to be wider than the width of the strut in the high stress regions. If a high radiopaque material is utilized and reduced radiopacity is desired, the width of the strut in the low stress region of the stent can be designed to be narrower than the strut width in the high stress regions. The end rings of the stent are strengthened by utilizing a plurality of W-shaped members having a strut construction which increases the overall hoop-strength of the ring.

16 Claims, 4 Drawing Sheets

U.S. PATENT DOCUMENTS

| | | |
|---|---|---|
| 4,553,545 A | 11/1985 | Maass et al. |
| 4,580,568 A | 4/1986 | Gianturco |
| 4,619,246 A | 10/1986 | Molgaard-Nielsen et al. |
| 4,649,922 A | 3/1987 | Wiktor |
| 4,650,466 A | 3/1987 | Luther |
| 4,655,771 A | 4/1987 | Wallsten |
| 4,681,110 A | 7/1987 | Wiktor |
| 4,706,671 A | 11/1987 | Weinrib |
| 4,725,334 A | 2/1988 | Brimm |
| 4,728,328 A | 3/1988 | Hughes et al. |
| 4,733,665 A | 3/1988 | Palmaz |
| 4,739,762 A | 4/1988 | Palmaz |
| 4,740,207 A | 4/1988 | Kreamer |
| 4,762,128 A | 8/1988 | Rosenbluth |
| 4,767,418 A | 8/1988 | Deininger et al. |
| 4,776,337 A | 10/1988 | Palmaz |
| 4,795,458 A | 1/1989 | Regan |
| 4,800,882 A | 1/1989 | Gianturco |
| 4,830,003 A | 5/1989 | Wolff et al. |
| 4,848,343 A | 7/1989 | Wallsten et al. |
| 4,856,516 A | 8/1989 | Hillstead |
| 4,870,966 A | 10/1989 | Dellon et al. |
| 4,877,030 A | 10/1989 | Beck et al. |
| 4,878,906 A | 11/1989 | Lindemann et al. |
| 4,886,062 A | 12/1989 | Wiktor |
| 4,892,539 A | 1/1990 | Koch |
| 4,893,623 A | 1/1990 | Rosenbluth |
| 4,907,336 A | 3/1990 | Gianturco |
| 4,913,141 A | 4/1990 | Hillstead |
| 4,922,905 A | 5/1990 | Strecker |
| 4,943,346 A | 7/1990 | Mattelin |
| 4,950,227 A | 8/1990 | Savin et al. |
| 4,963,022 A | 10/1990 | Sommargren |
| 4,969,458 A | 11/1990 | Wiktor |
| 4,969,890 A | 11/1990 | Sugita et al. |
| 4,986,831 A | 1/1991 | King et al. |
| 4,990,155 A | 2/1991 | Wilkoff |
| 4,994,071 A | 2/1991 | MacGregor |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,059,211 A | 10/1991 | Stack et al. |
| 5,061,275 A | 10/1991 | Wallsten et al. |
| 5,062,829 A | 11/1991 | Pryor et al. |
| 5,064,435 A | 11/1991 | Porter |
| 5,071,407 A | 12/1991 | Termin et al. |
| 5,073,694 A | 12/1991 | Tessier et al. |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,416 A | 4/1992 | Ryan et al. |
| 5,108,417 A | 4/1992 | Sawyer |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,158,548 A | 10/1992 | Lau et al. |
| 5,161,547 A | 11/1992 | Tower |
| 5,163,958 A | 11/1992 | Pinchuk |
| 5,171,262 A | 12/1992 | MacGregor |
| 5,180,368 A | 1/1993 | Garrison |
| 5,183,085 A | 2/1993 | Timmermans |
| 5,192,297 A | 3/1993 | Hull |
| 5,192,307 A | 3/1993 | Wall |
| 5,195,984 A | 3/1993 | Schatz |
| 5,197,978 A | 3/1993 | Hess |
| 5,222,971 A | 6/1993 | Willard et al. |
| 5,226,913 A | 7/1993 | Pinchuk |
| 5,234,456 A | 8/1993 | Silvestrini |
| 5,242,452 A | 9/1993 | Inoue |
| 5,282,823 A | 2/1994 | Schwartz et al. |
| 5,282,824 A | 2/1994 | Gianturco |
| 5,290,305 A | 3/1994 | Inoue |
| 5,292,331 A | 3/1994 | Boneau |
| 5,304,200 A | 4/1994 | Spaulding |
| 5,314,444 A | 5/1994 | Gianturco |
| 5,314,472 A | 5/1994 | Fontaine |
| 5,330,500 A | 7/1994 | Song |
| 5,344,425 A | 9/1994 | Sawyer |
| 5,354,308 A | 10/1994 | Simon et al. |
| 5,356,433 A | 10/1994 | Rowland et al. |
| 5,366,504 A | 11/1994 | Andersen et al. |
| 5,383,892 A | 1/1995 | Cardon et al. |
| 5,395,390 A | 3/1995 | Simon et al. |
| 5,421,955 A | 6/1995 | Lau et al. |
| 5,423,885 A | 6/1995 | Williams |
| 5,449,373 A | 9/1995 | Pinchasik et al. |
| 5,514,154 A | 5/1996 | Lau et al. |
| 5,527,324 A | 6/1996 | Krantz et al. |
| 5,569,295 A | 10/1996 | Lam |
| 5,601,593 A | 2/1997 | Freitag |
| 5,617,878 A | 4/1997 | Taheri |
| 5,630,829 A | 5/1997 | Lauterjung |
| 5,636,641 A | 6/1997 | Fariabi |
| 5,421,955 A | 1/1998 | Lau et al. |
| 5,707,388 A | 1/1998 | Lauterjung |
| 5,716,393 A | 2/1998 | Lindenberg et al. |
| 5,741,327 A | 4/1998 | Frantzen |
| 5,759,192 A | 6/1998 | Saunders |
| 5,776,161 A | 7/1998 | Globerman |
| 5,810,868 A | 9/1998 | Lashinski et al. |
| 5,836,966 A | 11/1998 | St. Germain |
| 5,843,120 A | 12/1998 | Israel et al. |
| 5,868,783 A | 2/1999 | Tower |
| 5,913,895 A | 6/1999 | Burpee et al. |
| 5,922,020 A * | 7/1999 | Klein et al. .................. 623/1.5 |
| 5,938,697 A | 8/1999 | Killion et al. |
| 6,017,365 A * | 1/2000 | Von Oepen ................ 623/1.15 |
| 6,027,526 A | 2/2000 | Limon et al. |
| 6,042,597 A | 3/2000 | Kveen et al. |

FOREIGN PATENT DOCUMENTS

| | | | |
|---|---|---|---|
| EP | 0221570 | A2 | 5/1987 |
| EP | 0335341 | B1 | 10/1989 |
| EP | 0338816 | A2 | 10/1989 |
| EP | 0357003 | A2 | 3/1990 |
| EP | 0361192 | A3 | 4/1990 |
| EP | 0364787 | A1 | 4/1990 |
| EP | 0372789 | A3 | 6/1990 |
| EP | 0380668 | B1 | 8/1990 |
| EP | 0407951 | A2 | 1/1991 |
| EP | 0421729 | A2 | 4/1991 |

| | | |
|---|---|---|
| EP | 0423916 A1 | 4/1991 |
| EP | 0428479 B1 | 5/1991 |
| EP | 0517075 B1 | 12/1992 |
| EP | 0540290 B1 | 5/1993 |
| EP | 0541443 A1 | 5/1993 |
| EP | 0 606 165 A1 | 7/1994 |
| EP | 0 688 545 A1 | 12/1995 |
| EP | 0 800 801 A1 | 10/1997 |
| EP | 0 806 190 A1 | 11/1997 |
| FR | 2677872 | 12/1992 |
| GB | 2070490 A | 9/1981 |
| GB | 2135585 A | 9/1984 |
| JP | SHO58-501458 | 9/1983 |
| JP | 62 231657 | 10/1987 |
| JP | 62235496 A | 10/1987 |
| JP | SHO63-214264 | 9/1988 |
| JP | 01083685 A | 3/1989 |
| JP | 1-299550 | 12/1989 |
| JP | HEI02-174859 | 7/1990 |
| JP | HEI02-255157 | 10/1990 |
| JP | 3-9745 | 1/1991 |
| JP | 03009746 A | 1/1991 |
| JP | 3-151983 | 6/1991 |
| JP | HEI04-25755 | 2/1992 |
| WO | WO91/07139 | 5/1991 |
| WO | WO92/06734 | 4/1992 |
| WO | WO92/09246 | 6/1992 |
| WO | WO 94/17754 | 8/1994 |
| WO | WO 95/23563 | 9/1995 |
| WO | WO 95/26695 | 10/1995 |
| WO | WO 96/09013 | 3/1996 |
| WO | WO97/25937 | 7/1997 |
| WO | WO98/20927 | 5/1998 |
| WO | WO 98/22159 | 5/1998 |
| WO | WO98/32412 | 7/1998 |
| WO | WO 98/58600 | 12/1998 |
| WO | WO99/17680 | 4/1999 |
| WO | WO99/39661 | 8/1999 |

OTHER PUBLICATIONS

Rösch, Josef, M.D., et al., Modified Gianturco Expandable Wrie Stents in Experimental and Clinical Use, *Annales de Radiologie*, pp. 100–103, vol. 31, No. 2, 1998.

Lawrence, David D., Jr., et al., Percutaneous Endovascular Graft: Experimental Evaluation, *Radiology*, pp. 357–360, vol. 163, May 1987.

Rösch, Josef, et al., Gianturco Expandable Stents in Experimental and Clinical Use, pp. 121–124. Twelfth Annual Course on "Diagnostic Angiography and Interventional Radiology" Mar. 23–26, 1987, San Diego, California.

Dotter, Charles T., Transluminally Placed Coilspring Endarterial Tube Grafts, *Investigative Radiology*, pp. 329–332, Sep./Oct. 1969.

Rösh, J., M.D., et al., Transjugular Intrahepatic Portacaval Shunt: An Experimental Work, *The American Journal of Surgery*, pp. 588–592, vol. 121, May 1971.

Dotter, Charles T., Transluminal Expandable Nitinol Coil Stent Grafting: Preliminary Report, *Radiology Journal*, pp. 259–260, Apr. 1983.

Cragg, et al., Non–Surgical Placement of Arterial Endoprostheses: A New Technique Using Nitinol Wire, *Radiology Journal*, pp. 261–263, Apr. 1983.

Maas, et al., Radiological Follow–Up of Transluminally Inserted Vascular Endoprostheses; An Experimental Study Using Expanding Spirals, *Radiology Journal*, pp. 659–663, 1984.

70th Scientific Assembly and Annual Meeting: Scientific Program, *Radiology*, Washington, DC: Nov. 25–30, 1084, Special Edition, vol. 153(P).

C. R. Bard, PE Plus Peripheral Balloon Dilatation Catheter, *C. R. Bard, Inc.*, Aug. 1985.

Wright, et al., Percutaneous Endovascular Stents: An Experimental Evaluation, *Radiology Journal*, pp. 69–72, 1985.

Palmaz, et al., Expandable Intraluminal Graft; A Preliminary Study, *Radiology Journal*, pp. 73–77, 1985.

Program: Day 2 (Nov. 18) The Radiological Society of North America, *Radiology*, 1985.

Charnsangavej, C., M.D., et al., Endovascular Stent for Use in Aortic Dissection: An in Vitro Experiment, *Radiology*, pp. 323–324, vol. 157, No. 2, Nov. 1985.

Wallace, Michael J., et al., Tracheobronchial Tree: Expandable Metallic Stents Used in Experimental and Clinical Applications (Work in Progress), *Radiology*, pp. 309–312, vol. 158, Feb. 1986.

72nd Scientific Assembly and Annual Meeting: RSNA Scientific Program, *Radiology*, Chicago: Nov. 30–Dec. 5, 1986, Special Edition vol. 161(P).

Duprat, et al., Flexible Balloon–Expanded Stent for Small Vessels, *Radiology Journal*, pp. 276–278, 1987.

Rösch, Josef, M.D., et al., Gianturco Expandable Stents in Experimental and Clinical Use, paper presented at The Twelfth Annual Course on "Diagnostic Angiography and Interventional Radiology" Mar. 23–26, 1987 (San Diego, California).

Rösch, Joseph, M.D., et al., Gianturco Expandable Wire Stents in the Treatment of Superior Vena Cava Syndrome Recurring After Maximum–Tolerance Radiation, *Cancer*, pp. 1243–1246, vol. 60, Sep. 1987.

Yoshioka, Tetsuya, et a., Self–Expanding Endovascular Graft: An Experimental Study in Dogs, *American Journal of Roentgeriology*, pp. 673–676, vol. 151, Oct. 1988.

Yoshioka, et al., Developemnt and Clinical Application of Biliary Endoprostheses Using Expandable Metallic Stents, *Japan Radiological Society*, 1988, vol. 48, No. 9, pp. 1183–1185 (with translation).

Mirich, et al., "Percutaneously Placed Endovascular Grafts for Aortic Aneurysms: Feasibility Study", *Radiology*, 1989, Part 2, pp. 1033–1037.

\* cited by examiner

STENT DESIGN WITH END RINGS HAVING ENHANCED STRENGTH AND RADIOPACITY

BACKGROUND OF THE INVENTION

The present invention relates to expandable endoprosthesis devices, generally called stents, which are adapted to be implanted into a patient's body lumen, such as a blood vessel, to maintain the patency thereof. Stents are particularly useful in the treatment and repair of blood vessels after a stenosis has been compressed by percutaneous transluminal coronary angioplasty (PTCA), percutaneous transluminal angioplasty (PTA), or removed by atherectomy or other means, to help improve the results of the procedure and reduce the possibility of restenosis.

Stents are generally cylindrically shaped devices which function to hold open and sometimes expand a segment of a blood vessel or other arterial lumen, such as coronary artery. Stents are usually delivered in a compressed condition to the target site and then deployed at that location into an expanded condition to support the vessel and help maintain it in an open position. They are particularly suitable for use in supporting and holding back a dissected arterial lining which can occlude the fluid passageway there through.

A variety of devices are known in the art for use as stents and have included coiled wires in a variety of patterns that are expanded after being placed intraluminally on a balloon catheter; helically wound coiled springs manufactured from an expandable heat sensitive metal; and self-expanding stents inserted into a compressed state for deployment into a body lumen. One of the difficulties encountered in using prior art stents involve maintaining the radial rigidity needed to hold open a body lumen while at the same time maintaining the longitudinal flexibility of the stent to facilitate its delivery and accommodate the often tortuous path of the body lumen.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanium (NiTi) alloys, which will automatically expand from a compressed state when the stent is advanced out of the distal end of the delivery catheter into the body lumen. Such stents manufactured from expandable heat sensitive materials allow for phase transformations of the material to occur, resulting in the expansion and contraction of the stent.

Details of prior art expandable stents can be found in U.S. Pat. No. 3,868,956 (Alfidi et al.); U.S. Pat. No. 4,512,1338 (Balko et al.); U.S. Pat. No. 4,553,545 (Maass, et al.); U.S. Pat. No. 4,733,665 (Palmaz); U.S. Pat. No. 4,762,128 (Rosenbluth); U.S. Pat. No. 4,800,882 (Gianturco); U.S. Pat. No. 5,514,154 (Lau, et al.); U.S. Pat. No. 5,421,955 (Lau et al.); U.S. Pat. No. 5,603,721 (Lau et al.); U.S. Pat. No. 4,655,772 (Wallsten); U.S. Pat. No. 4,739,762 (Palmaz); and U.S. Pat. No. 5,569,295 (Lam), which are hereby incorporated by reference.

Further details of prior art self-expanding stents can be found in U.S. Pat. No. 4,580,568 (Gianturco); and U.S. Pat. No. 4,830,003 (Wolff, et al.), which are hereby incorporated by reference.

Expandable stents are delivered to the target site by delivery systems which often use balloon catheters as the means for expanding the stent in the target area. One such stent delivery system is disclosed in U.S. Pat. No. 5,158,548 to Lau et al. Such a stent delivery system has an expandable stent in a contracted condition placed on an expandable member, such as an inflatable balloon, disposed on the distal portion of an elongated catheter body. A guide wire extends through an inner lumen within the elongated catheter body and out its distal end. A tubular protective sheath is secured by its distal end to the portion of the guide wire which extends out of the distal end of the catheter body and fits over the stent mounted on the expandable member on the distal end of the catheter body.

Some prior art stent delivery systems for implanting self-expanding stents include an inner lumen upon which the compressed or collapsed stent is mounted and an outer restraining sheath which is initially placed over the compressed stent prior to deployment. When the stent is to be deployed in the body vessel, the outer sheath is moved in relation to the inner lumen to "uncover" the compressed stent, allowing the stent to move to its expanded condition into the target area.

The positioning of the stent at the desired location in the body lumen is often critical since inaccurate placement can affect the performance of the stent and the success of the medical procedure. The positioning of the stent before, during, and after its implantation and expansion is generally monitored by external monitoring equipment, such as a fluoroscope, which allows the physician to place the stent in the exact target site. Radiopaque markers placed on the ends of the catheters of the stent delivery system often are utilized to help locate the stent on the catheter during deployment. Additionally, the stent itself can be made from a radiopaque material. For this reason, it is desirable for the stent to be moderately radiopaque. Stents which lack sufficient radiopacity are usually more difficult to position accurately and assess with angiography. Therefore, even a physician using the best available stent delivery systems may not be capable of accurately positioning the stent if there are problems visualizing the stent on the fluoroscope.

Currently, many stents in use are formed from stainless steel or nickel-titanium type alloys which are not always readily visible on the medical imaging instrument. With these materials, the radiopacity of the stent is highly dependant on the amount of metal in the stent. Stents which have thicker struts are generally more radiopaque than stents with thinner struts. However, the strut of the stent cannot be too thick or wide, since the stent must be capable of expanding radially to a larger diameter during deployment. Generally, stents having wider struts are more radiopaque then stents with narrower struts, however, if the strut width is increased in areas subject to high stresses, the strain created in the material at these areas could increase dramatically and may cause cracks in the stent to form, which is highly undesirable.

To increase radiopacity, radiopaque markers have been placed on stents to attempt to provide a more identifiable image for the physician. One such surgical stent featuring radiopaque markers is disclosed in U.S. Pat. No. 5,741,327 (Frantzen) which utilizes radiopaque marker elements attached to the ends of a radially expandable surgical stent to increase the visibility of the stent. However, there are certain drawbacks in utilizing radiopaque markers since some markers may restrict the ability of the stent to fully expand radially and can cause an unwanted protrusion from the surface of the stent which can possibly pierce the wall of the body lumen. Additionally, radiopaque markers can either fail to provide an adequate outline of the stent or illuminate the stent so brightly that fine details such as blood vessels or other bodily structures are obscured when an image is obtained. When the stent is made from highly radiopaque metals such as tantalum or platinum, often the radiopacity of the stent is too high and there is a need to decrease the radiopacity to allow adequate visualization of the surrounding blood vessels, especially at the target location where the PCTA or the PTA procedure has been performed.

The design of the strut pattern of the stent can sometimes lead to unwanted complications during the stent deployment. For example, in some instances, the forces of the body lumen on the fully expanded stent can cause the ends of the stent to collapse somewhat causing the stent to take the form of a "cigar" shape, which is highly undesirable. This formation of a "cigar" shape is attributable to the fact that the ends of some stents are often not as strong and well supported as the middle section of the stent. Therefore, when the stent is deployed within the body lumen and has a force applied to it, the end portions can compress somewhat before there is any appreciable compression of the middle section of the stent, resulting in the formation of the "cigar" shape. This formation of a "cigar" shape can lead to abnormal blood flow through the stent, which can cause the formation of unwanted thrombosis, which will be released into the blood stream. A stent design which forms a uniform inner passage way is less likely to cause the formation of thrombosis or blood clots in the bloodstream, and therefore it is highly desirable to have a stent design which has sufficient strength along its entire length to prevent the formation of this unwanted "cigar" shape.

What has been needed is a stent which has a high degree of flexibility so it can be advanced through tortuous passageways of the anatomy and can be expanded to its maximum diameter, yet has sufficient strength along its entire length to create a uniform inner-passage for blood flow and provides sufficient radiopacity to present a clear image on a fluoroscope or other medical imaging device during deployment. Such a stent should have sufficient strength and radiopaque properties, yet be configured in a manner which facilitates its manufacture using known manufacturing techniques and utilizes conventional stent delivery systems for implantation in the target location. Moreover, such a stent would be beneficial if it can be manufactured from biocompatible materials which are presently being used in stent designs.

SUMMARY OF INVENTION

The present invention is directed to stents having strut patterns which enhance the strength of the ends of the stent and the overall radiopacity of the stent, yet retain high longitudinal flexibility along their longitudinal axis to facilitate delivery through tortuous body lumens and remain stable when expanded radially to maintain the patency of a body lumen, such as an artery or other vessel, when implanted therein. The present invention in particular relates to stents with unique end portions having sufficient hoop strength to maintain a constant inner diameter which prevents the stent from taking on a "cigar" shape when deployed in the body lumen. The unique end rings of the present invention are particularly useful on self-expanding stents which may otherwise have end rings that may be more susceptible to compression forces. The present invention also relates to the control of the radiopacity of a stent by varying the strut geometry along the stent. By making the width of the strut either wider or narrower in different regions of the stent, the properties of the stent can be customized for a particular application in order to achieve the desired amount of strength and radiopacity for the stent.

Depending upon the strut pattern of the particular stent, there are usually regions or areas of the stent which experience high stresses (referred to as high stress regions) when the strut is expanded radially during deployment. There are other areas or regions of the stent which experience low stresses (referred to as low stress regions) in which stresses on the stent are much lower and any changes in the width of the strut in this region would not dramatically alter the strain and other mechanical properties of the stent. Depending on the material selected for the stent, the width of the stent in the low stress regions can be either increased or reduced in order to change the overall radiopacity of the stent. For example, if a material such as stainless steel or Nitinol is used, the overall radiopacity of the stent can be increased by increasing the width of the strut in the low stress regions. If a high radiopaque material such as tantalum or platinum is used, it is possible to decrease the width of the strut in the low stress regions to decrease the overall radiopacity of the stent, if necessary. In this manner, the addition or decrease of metal in the low stress regions of the strut will effect the overall radiopacity of the stent, yet will not affect the overall strength and mechanical properties of the stent.

Each of the different embodiments of stents of the present invention include a plurality of adjacent cylindrical elements (also known as or referred to as "rings") which are generally expandable in the radial direction and arranged in alignment along a longitudinal stent axis. The cylindrical elements are formed in a variety of serpentine wave patterns transverse to the longitudinal axis and contain a plurality of alternating peaks and valleys. At least one interconnecting member extends between adjacent cylindrical elements and connects them to one another. These interconnecting members insure a minimal longitudinal contraction during radial expansion of the stent in the body vessel. The serpentine patterns have varying degrees of curvature in the regions of peaks and valleys and are adapted so that radial expansion of the cylindrical elements are generally uniform around their circumferences during expansion of the stent from their contracted conditions to their expanded conditions.

Generally, these peaks and valleys of the cylindrical element are subject to high stresses during expansion due to the geometry of the cylindrical element. These valleys and peaks constitute the aptly-named high stress regions of the stent which are susceptible to stress fractures during expansion. For this reason, the width of the strut in the peak and valley portions of the cylindrical element should remain relatively fixed and uniform so that high stresses will not be concentrated in any one particular region of the pattern, but will be more evenly distributed along the peaks and valleys, allowing them to expand uniformly. The regions of the cylindrical element between the peaks and valleys generally form the low stress regions of the stent which do not experience high stresses and strains during radial expansion, thus allowing the width of the stent in these regions to be varied in order to increase or decrease the radiopacity of the stent, as needed, depending upon the material used to manufacture the stent. Generally, these low stress regions extending between the peaks and valleys of the cylindrical element are linear segments which are not subject to high stresses during radial expansion. An increase or decrease of the width of the strut in these low stress regions of the cylindrical element generally will not alter the overall mechanical properties of the stent.

The elongated interconnecting members which connect adjacent cylindrical elements may also have an increase or decrease in strut width in order to change the radiopacity of the stent. In one preferred embodiment, the interconnecting element has a tapered configuration in which one end of the interconnecting member is wider than the other end and tapers from end to end to increase the amount of material, and hence, the radiopacity of the stent. The number and location of the interconnecting members can be varied as may be needed. Generally, the greater the longitudinal flexibility of the stents, the easier and more safely they can be delivered to the implantation site, especially where the implantation site is on a curve section of a body lumen, such as a coronary artery or peripheral blood vessel.

In one particular embodiment of the present invention, the end rings of the stent include peaks and valleys which are made with multiple W or double-curved shapes which enhance both the hoop strength of the stent, along with the radiopacity at the ends of the stent. In this particular embodiment of the invention, the width of the strut in the low-stress regions of the double-curved portion of the cylindrical rings is increased to increase the amount of material at the ends of the stent to enhance radiopacity. This increase in the amount of material at the ends provides satisfactory visibility when one attempts to locate the stent on the fluoroscope. The increase in the mass of the end rings also helps increase the overall strength of the ends of the stent, which helps prevent the stent from collapsing to a "cigar" shape during deployment.

The resulting stent structures are a series of radially expandable cylindrical elements that are spaced longitunally close enough so that small dissections in the wall of a body lumen may be pressed back into position against the lumenal wall, but not so close as to compromise the longitudinal flexibility of the stent both when negotiating through the body lumens in their unexpanded state and when expanded into position. Each of the individual cylindrical elements may rotate slightly relate to their adjacent cylindrical elements without significant deformation, cumulatively providing stents which are flexible along their length and about their longitudinal axis, but which still are very stable in their radial direction in order to resist collapse after expansion. An increase or decrease of the strut width in the low stress regions of the stent provides the necessary amount of radiopacity to allow the stent to be adequately visualized on the external monitoring equipment.

The stent of the present invention can be directed to both balloon expandable or self-expanding stent designs. The technique of the present invention can also be applied to virtually any type of stent design. However, it is most easily applied to laser cut stents made from tubing.

The stents of the present invention can be readily delivered to the desired target location by mounting them on an expandable member, such as a balloon, of a delivery catheter and passing the catheter-stent assembly lumen to the target area. A variety of means for securing the stent to the extendible member of the catheter for delivery to the desired location are available. It is presently preferred to crimp or compress the stent onto the unexpanded balloon. Other means to secure the stent to the balloon included providing ridges or collars on the inflatable member to restrain lateral movement, using bioabsorbable temporary adhesives, or adding a retractable sheath to cover the stent during delivery through the body lumen. When a stent of the present invention is made from a self expanding material such as nickel titanium alloy, a suitable stent delivery assembly which includes a retractable sheath, or other means to hold the stent in its expanded condition prior to deployment, can be utilized.

The serpentine pattern of the individual cylindrical elements can optionally be in phase with each other in order to reduce the contraction of the stent along their length when expanded. The cylindrical elements of the stent are plastically deformed when expanded (except with NiTi alloys) so that the stent will remain in the expanded condition and therefore must be sufficiently rigid when expanded to prevent the collapse thereof during use.

In stents formed from super elastic nickel titanium alloys, the expansion occurs when the stress of compression is removed. This allows the phase transformation from martensite back to austenitite to occur, and as a result the stent expands.

One approach to a stent design which relates to the control of stent strength by varying strut geometry along the length of the stent is disclosed in my co-pending application Ser. No. 09/298,063, filed Apr. 22, 1999, by Daniel L. Cox and Timothy A. Limon entitled "Variable Strength Stent," whose contents are hereby incorporated by reference. In that approach, the strength of the stent was enhanced by increasing the length or width of the strut of the cylindrical elements to increase the mass and resulting mechanical strength of the stent. In that approach, certain cylindrical elements having wider struts are located, for instance, in the middle or center section of the stent, while cylindrical elements having narrower strut widths are placed at the ends of the stent to avoid the formation of a "dog bone" shape during deployment. However, in this earlier approach, the entire width of the strut in each cylindrical element or ring is maintained uniform throughout, regardless of whether the cylindrical element has a wider or narrower strut pattern. In my present invention described herein, the width of the strut in high and low stress regions of the cylindrical ring is varied accordingly to achieve the desired strength and radiopacity which is needed.

These and other features and advantages of the present invention will become more apparent from the following detailed description of the invention, when taken in conjunction with the accompanying exemplary drawings.

DETAILED DESCRIPTION OF THE PREFERRED EMBODIMENTS

Prior art stent designs, such as the MultiLink Stent™ manufactured by Advanced Cardiovascular Systems, Inc., Santa Clara, Calif., include a plurality of cylindrical rings that are connected by three connecting members between adjacent cylindrical rings. Each of the cylindrical rings is formed of a repeating pattern of U-, Y-, and W-shaped members, typically having three repeating patterns forming each cylindrical element or ring. A more detailed discussion of the configuration of the MultiLink Stent™ can be found in U.S. Pat. No. 5,569,295 (Lam) and U.S. Pat. No. 5,514,154 (Lau et al.), whose contents are hereby incorporated by reference.

Figure 1:
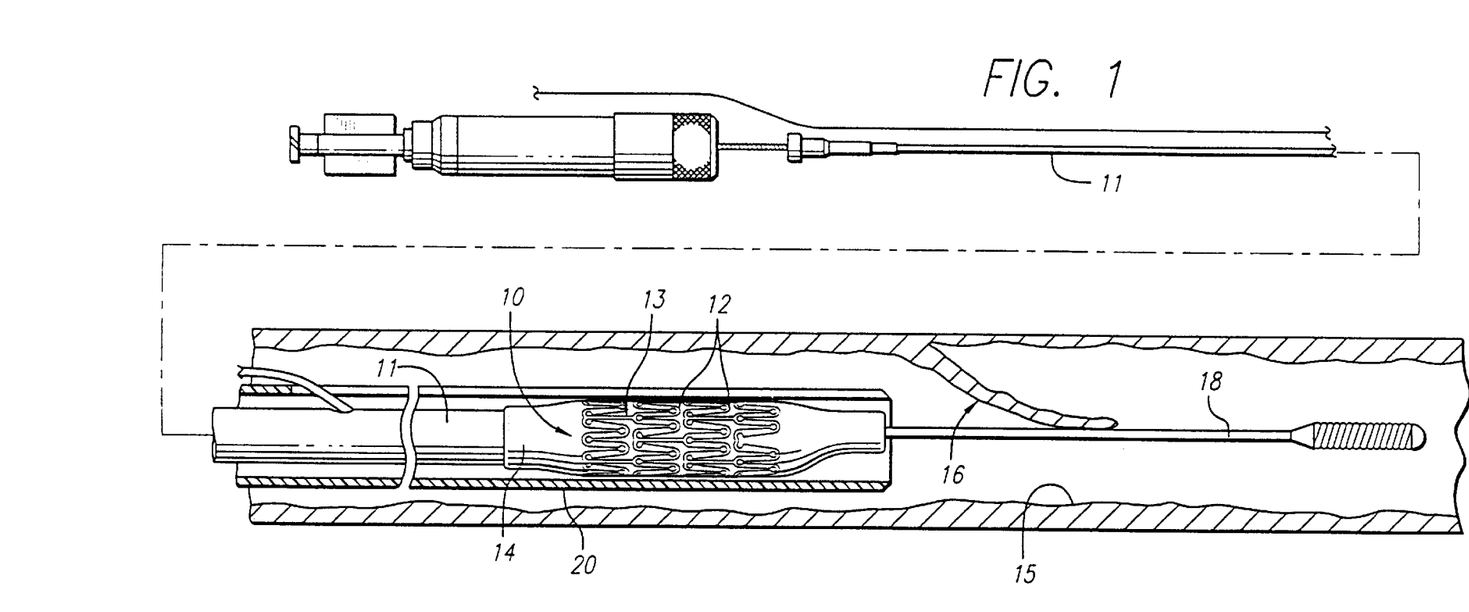
FIG. 1 is an elevational view, partially in section, depicting the stent embodying features of the present invention mounted on a delivery catheter disposed within a vessel.
Figure 5:
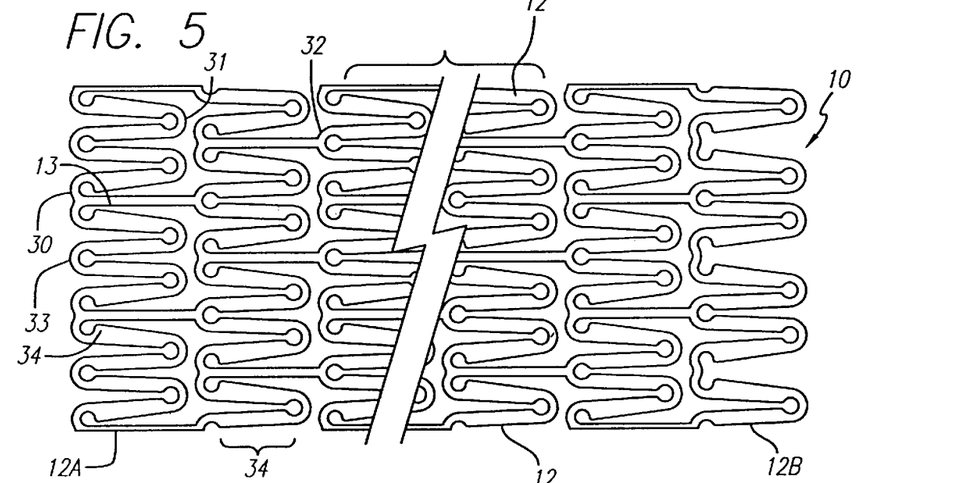
FIG. 5 is plan view of a preferred embodiment of a flattened stent of the present invention, which illustrates the serpentine pattern including peaks and valleys which form the cylindrical elements of the stent and include regions having wider struts in low stress regions and narrower struts in high stress regions.

Beyond those prior art stents, FIG. 1 illustrates an exemplary embodiment of stent 10 incorporating features of the present invention, which stent is mounted onto delivery catheter 11. FIG. 5 is a plan view of this exemplary embodiment stent 10 with the structure flattened out into two dimensions to facilitate explanation. Stent 10 generally comprises a plurality of radially expandable cylindrical elements 12 disposed generally coaxially and interconnected by interconnecting members 13 disposed between adjacent cylindrical elements 12. The delivery catheter 11 has an expandable portion or balloon 14 for expanding stent 10 within artery 15 or other vessel. The artery 15, as shown in FIG. 1, has a dissected or detached lining 16 which has occluded a portion of the arterial passageway.

The delivery catheter 11 onto which stent 10 is mounted is essentially the same as a conventional balloon dilatation catheter for angioplasty procedures. The balloon 14 may be formed of suitable materials such as polyethylene, polyethylene terephthalate, polyvinyl chloride, nylon and, ionomers such as Surlyn® manufactured by the Polymer Products Division of the Du Pont Company. Other polymers may also be used.

In order for stent 10 to remain in place on balloon 14 during delivery to the site of the damage within artery 15, stent 10 is compressed or crimped onto balloon 14. A retractable protective delivery sleeve 20 may be provided to ensure that stent 10 stays in place on balloon 14 of delivery catheter 11 and to prevent abrasion of the body lumen by the open surface of stent 10 during delivery to the desired arterial location. Other means for securing stent 10 onto balloon 14 also may be used, such as providing collars or ridges on the ends of the working portion, i.e., the cylindrical portion, of balloon 14. Each radially expandable cylindrical element 12 of stent 10 may be independently expanded. Therefore, balloon 14 may be provided with an inflated shape other than cylindrical, e.g., tapered, to facilitate implantation of stent 10 in a variety of body lumen shapes. When the stent 10 is made from a self-expanding material such as Nitinol, a suitable delivery device with retractable sleeve may be used to display the stent.

Figure 2:
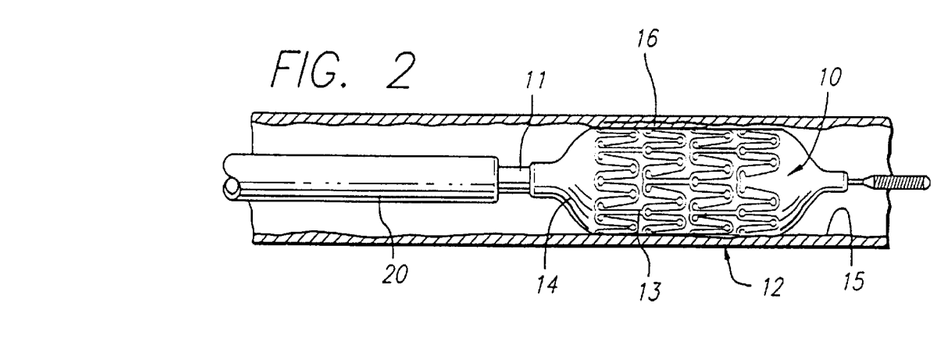
FIG. 2 is an elevational view, partially in section, similar to that shown in FIG. 1, wherein the stent is expanded within a vessel, pressing the lining against the vessel wall.

In one preferred embodiment, the delivery of stent 10 is accomplished in the following manner. Stent 10 is first mounted onto inflatable balloon 14 on the distal extremity of delivery catheter 11. Stent 10 may be crimped down onto balloon 14 to obtain a low profile. The catheter-stent assembly can be introduced within the patient's vasculature in a conventional Seldinger technique through a guiding catheter (not shown). Guidewire 18 is disposed through the damaged arterial section with the detached or dissected lining 16. The catheter-stent assembly is then advanced over guide wire 18 within artery 15 until stent 10 is directly under detached lining 16. Balloon 14 of catheter 11 is inflated or expanded, thus expanding stent 10 against the inside of artery 15, which is illustrated in FIG. 2. While not shown in the drawing, artery 15 is preferably expanded slightly by the expansion of stent 10 to seat or otherwise embed stent 10 to prevent movement. Indeed, in some circumstances during the treatment of stenotic portions of an artery, the artery may have to be expanded considerably in order to facilitate passage of blood or other fluid there through.

Figure 3:
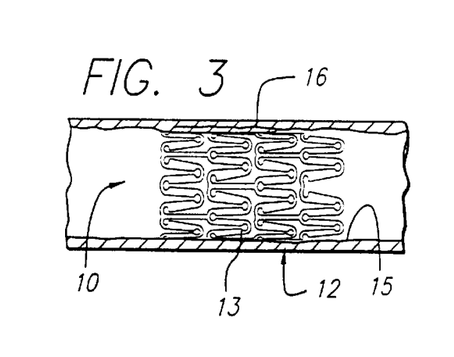
FIG. 3 is an elevational view, partially in section, showing the expanded stent within the vessel after withdrawal of the delivery catheter.

While FIGS. 1–3 depict a vessel having detached lining 16, stent 10 can be used for purposes other than repairing the lining. Those other purposes include, for example, supporting the vessel, reducing the likelihood of restenosis, or assisting in the attachment of a vascular graft (not shown) when repairing an aortic abdominal aneurysm.

In general, stent 10 serves to hold open artery 15 after catheter 11 is withdrawn, as illustrated in FIG. 3. Due to the formation of stent 10 from an elongated tubular body, the undulating component of the cylindrical elements of stent 10 is relatively flat in a transverse cross-section so that when stent 10 is expanded, cylindrical elements 12 are pressed into the wall of artery 15 and as a result do not interfere with the blood flow through artery 15. Cylindrical elements 12 of stent 10 that are pressed into the wall of artery 15 will eventually be covered with endothelial cell growth that further minimizes blood flow turbulence. The serpentine pattern of cylindrical sections 12 provide good tacking characteristics to prevent stent movement within the artery. Furthermore, the closely spaced cylindrical elements 12 at regular intervals provide uniform support for the wall of artery 15, and consequently are well adapted to tack up and hold in place small flaps or dissections in the wall of artery 15 as illustrated in FIGS. 2 and 3.

Figure 6:
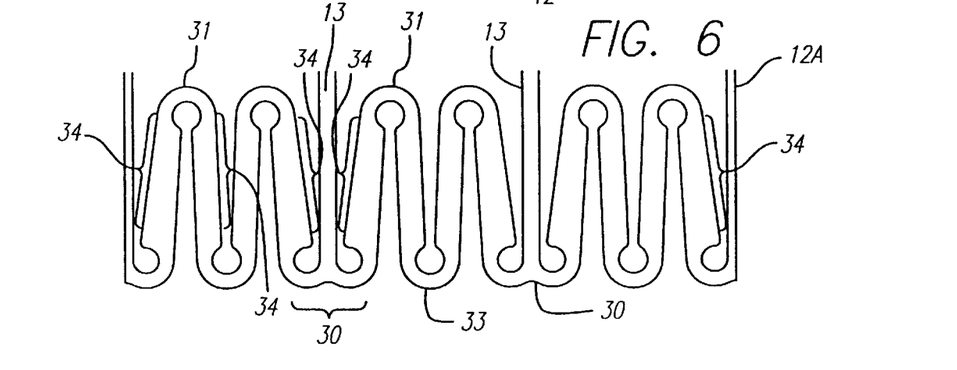
FIG. 6 is an enlarged partial view of the stent of FIG. 5 depicting one serpentine pattern along with the peaks and valleys which form one particular preferred embodiment of a cylindrical element of a stent made in accordance with the present invention.

The stresses involved during expansion from a low profile to an expanded profile are generally evenly distributed among the various peaks and valleys of stent 10. Referring to FIGS. 5 and 6, one preferred embodiment of the present invention as depicted in FIGS. 1–3 is shown wherein each expanded cylindrical element 12 embodies a serpentine pattern having a plurality of peaks and valleys that aid in the even distribution of expansion forces. In this exemplary embodiment, interconnecting members 13 serve to connect adjacent valleys of each adjacent cylindrical element 12 as described above. The various peaks and valleys generally have U, Y, W and inverted-U shapes, in a repeating pattern to form each cylindrical element 12. It should be appreciated that the cylindrical element 12 can be formed in different shapes without departing from the spirit and scope of the present invention.

Figure 4:
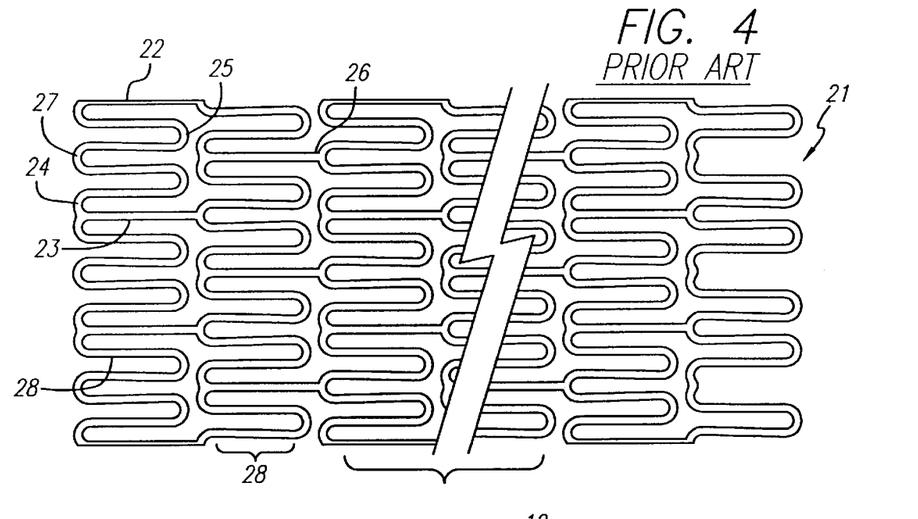
FIG. 4 is a plan view of a flattened stent of the prior art, which illustrates the uniform strut width of the cylindrical rings arranged along the stent.

Referring now to FIG. 4, a typical prior art stent 21 is shown which includes cylindrical elements or rings 22 which are connected by interconnecting members 23. FIG. 4 is a plan view of a prior art stent with the structure flattened out into two dimensions to facilitate explanation. Each cylindrical element 22 includes peaks and valleys generally having U, Y, W, and inverted-U shapes, in repeating patterns to form each individual element 22. The high stress regions of the prior art stent 21 include the double-curved portion (W) 24 located in the region of the valley where interconnecting member 23 is connected to an adjacent cylindrical element. The peak portion (inverted-U) 25 and valley portion (Y) 26 and valley portion (U) 27 are also considered high stress regions of the prior art stent. During radial expansion, these high stress regions experience high stresses and strains which can cause cracks to occur if the width of the strut is too wide. If the strut width were increased in these areas designated by the double-curved portion (W) 24, peak portion (U) 25, valley portion (Y) 26 and valley portion (U) 27, the strain in the material would increase dramatically and could cause cracks to occur, which is highly undesirable when deploying the stent in to the target region. Low stress regions of the prior art stent 21 include the linking portions 28 which extend between and connect the peak portions and valley portions on the cylindrical element 22. The linking portions 28 are generally linearly shaped and, as shown in FIG. 4, have widths which are uniform with the strut width found in the high stress regions of the stent 21. Similarly, the interconnecting member 23 defines a low stress region and extends from the top of the double-curved portion (W) 24 to the bottom of the valley portion (Y) 26 of the adjoining cylindrical element 21. Again, the stresses developed in these low stress regions during radial expansion are relatively low and a change in strut width would not dramatically alter the strain or overall mechanical properties of the stent.

During expansion, the double-curved portions (W) located in the region of the valley where interconnecting members 13 are connected have the most mass and, accordingly, are the stiffest structure during deformation. Peak portions (U) are less stiff and valley portions (Y) have intermediate stiffness.

By allocating the amount of mass to specific strength, it is possible to create a stent having variable strength, with greater strength at the high-mass areas of the strut. In this same fashion, the radiopacity of the stent can also be increased. Given a stent having a constant thickness in its struts, the increased mass is accomplished by increasing the width of the strut in the low-stress regions of the cylindrical element of the stent. The following exemplary embodiments apply this theory.

Referring again to FIGS. 5 and 6, the stent 10 includes cylindrical elements 12 having peaks and valleys with U, Y, W and inverted-U shapes in repeating patterns to form each individual cylindrical element 12. The high stress regions of this stent 10 include the double-curved portion (W) 30 located in the region of the valley where each interconnecting member 13 is connected to an adjacent cylindrical element 12. The peak portion (inverted-U) 31, the valley portion (Y) 32 and valley portion (U) 33 are also high stress regions of the stent 10. During radial expansion, these high stress regions experience high stresses and strains which can cause cracks to form in the stent if the width of the strut is too large. If the strut widths are increased in the areas designated by the double-curved portion (W) 30, peak portion (inverted-U) 31, valley portion (Y) 32 and valley portion (U) 33, the strain in the material would increase dramatically and could cause cracks to occur or may prevent the stent from fully deploying into its enlarged diameter during radial expansion, which is highly undesirable when deploying the stent 10 into the target region.

The stent 10 also has low stress regions which include linking portions 34 which extend between and connect the peak portions and valley portions of the cylindrical element 12. The linking portions 34 are generally linearly-shaped and, as is shown in the FIG. 6, have strut widths which are much larger than the strut width found in the adjacent high stress regions of the stent. The increase of the strut width in the linking portions 34 has only a small effect on the radial strength because the stress in this area is very low and does not carry much load. The strain is also unchanged because the curved areas of the peak portion (inverted-U) 31 and valley portion (Y) 32 and valley portion (U) 33) are narrower and correspond to the strut width shown in FIG. 4. The major effect of the wider strut in the linking portions 34 is in the overall radiopacity of the stent 10. The additional metal in these linking portions 34 increases the overall amount of metal in the stent and hence its radiopacity. In the crimped state, the stent 10 can be designed to have over 75% metal coverage.

The stent 10 shown in FIGS. 5 and 6 include a first and second end rings 12A and 12B. As is shown, the end ring 12A has interconnecting members 13 in each (W) or double-curved portion 30, to provide maximum support at the end of the stent. The added metal of the linking portion 34 of the double-curved portion 30 increases the overall amount of material at the end of the stent, and hence the stent's radiopacity and strength is increased. As a result, the end ring provides a stronger scaffolding which helps prevent the formation of a "cigar" shape during deployment. It should be appreciated that although the double-curved portion (W) is considered a high-stress region, it is the curved section 30 of the W that is susceptible to high stresses. The remaining portion of the W, namely, the two linking portions 34 (See FIG. 6), are low-stress regions which are not as susceptible to high stresses.

Figure 7:
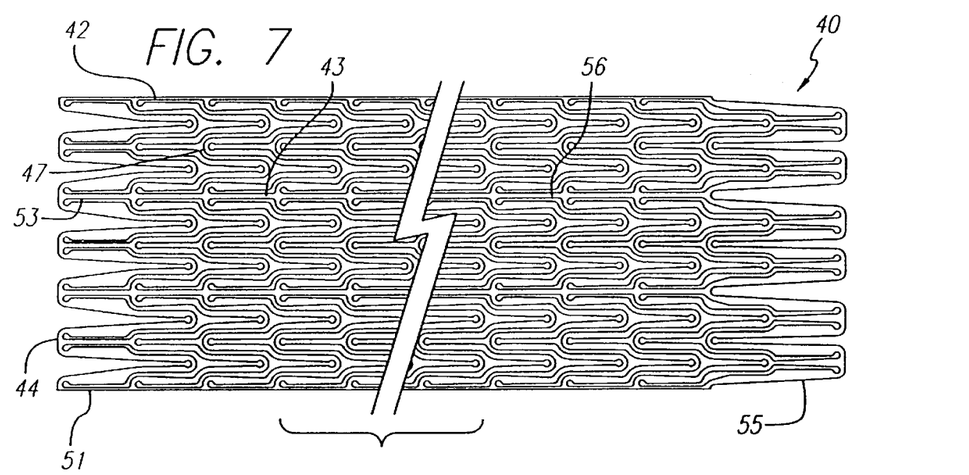
FIG. 7 is a plan view of an alternative preferred embodiment of a flattened stent of the present invention, which illustrates the serpentine pattern along with the peaks and valleys which form another preferred embodiment of a stent made in accordance with the present invention.
Figure 8:
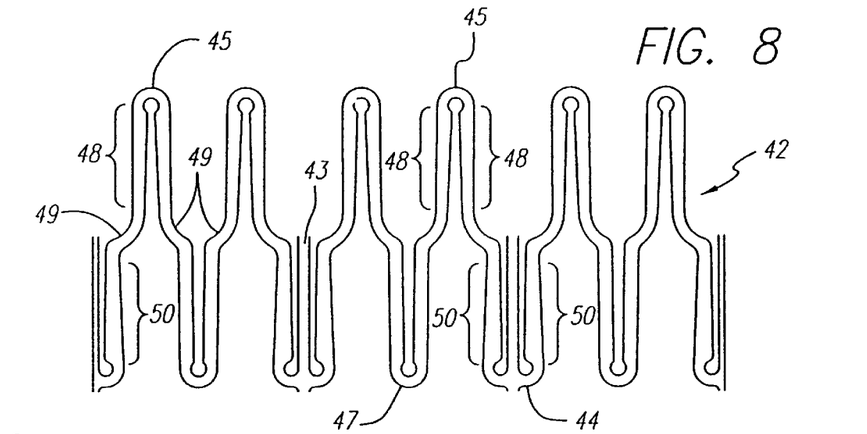
FIG. 8 is an enlarged partial view of the stent of FIG. 7 depicting the serpentine pattern along with the peaks and valleys which form one preferred embodiment of a cylindrical element made in accordance with the present invention.
Figure 9:
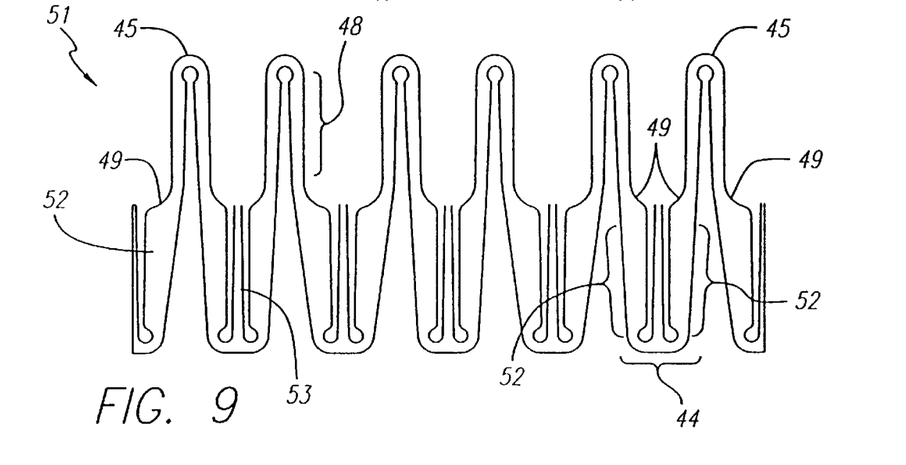
FIG. 9 is an enlarged partial view of the stent of FIG. 9 the serpentine pattern along with the peaks and valleys which form one preferred embodiment of a cylindrical element of the present invention which can be formed at the ends of the stent.

Referring now to FIGS. 7–9, another preferred embodiment of the present invention using the concept of increasing the strut width in low stress regions of the stent is shown. In this particular embodiment, the stent 40 includes cylindrical elements 42 which includes peaks and valleys having U, Y, W and inverted-U shapes, in repeating patterns to form each individual cylindrical element 42. Each cylindrical element 42 is connected to an adjacent cylindrical element via an interconnecting member 43. The high stress region of this stent 40 include the double-curved portion (W) 44, located in the region of valley where each interconnecting member 43 is connected to an adjacent cylindrical element 42. The peak portion (inverted-U) 45, and valley portion (U) 47 are also high stress regions of the stent. During radial expansion, these high stress regions experience high stresses and strains which can cause cracks to form in the stent if the width of the strut is too large. In the design of a stent of the present invention, the strut width is set in these high stress regions to meet the material strain, radial strength and expansile requirements of the stent. If the strut widths are increased in the areas designated by the double-curved portion (W) 44, peak portion (inverted-U) 45, and valley portion (U) 47, the strain in the material would increase dramatically and could cause cracks to occur or may prevent the stent from fully deploying to its larger diameter during radial expansion, which again is a highly undesirable occurrence when deploying the stent into a target region.

The stent 40 also has low stress regions which include linking portions 48 which extend from the peak portion (inverted-U) 45 to a shoulder portion 49 of the cylindrical element 42. This shoulder portion 49 can have a strut width which is reduced to allow the stent to be crimped to a very small profile. Additional linking portions 50 which extend between the valley portions and the shoulders 49 can also have increased strut width to enhance the overall radiopacity, with minimal effect on the overall mechanical properties or the profile of the stent.

In the particular stent design shown in FIGS. 7–9, the cylindrical elements formed at the ends of the stent can also be customized to enhance the radiopacity, along with the structural strength of the stent. Referring specifically to FIG. 9, the end cylindrical element or ring 51 has strut widths in the linking portions 52 which are much larger than the strut widths in the valley portion of the double-curved portion (W) 44. These particular linking portions 52 extend between the end of the double-curved portion (W) 44 up to the shoulder portion 49 in this particular cylindrical element 51. Again, the increase in the width thickness in the linking portions 52 both increases the radiopacity of the stent along with the strength at the end rings 51 and 55. The interconnecting members 53 shown in FIG. 9 also have increased strut width from the end which extends from the double-curved portion (W) 44 up to the adjacent valley portion (Y) 47. In this particular embodiment, the interconnecting members 53 are shown with struts having a tapered pattern which increases the overall strength of the stent at the end rings 51 and 55 of the stent 40. Additionally, the presence of additional interconnecting members 53 enhances the strength of the end rings 51 and 55 of the stent, as well as the radiopacity in this particular region of the stent. It should be appreciated that interconnecting members having a wider strut pattern could also be utilized in other areas of the stent, not necessarily just at the end rings 51 and 55 of the stent 40, if additional strength or radiopacity is desired.

In the particular embodiment of the present invention shown in FIGS. 7–9, the end rings 51 and 55 of the stent 40 includes six (W) or double-curved portions which increase the end strength of the stent. Since the (W) portion is usually the stiffest part of the cylindrical ring, after it is deployed it also provides the stiffest scaffolding structure which is beneficial in preventing the formation of the "cigar" shape after the stent is deployed. By utilizing three or more (W) portions with wide linking portions 52 on the end rings, the ends of the stent can be strengthened to help maintain a constant inner diameter of the stent and provide a smooth and continuous passageway for blood flow. The use of numerous (W) portions also greatly increases the radiopacity of the stent at the end regions which also helps identify and locate the stent when viewed by a fluoroscope.

In designing a stent in accordance with the present invention, the strut width in the low stress regions can be either increased or decreased to provide the necessary radiopacity for the stent. For example, if a low radiopaque material such as stainless steel or NiTi alloy is chosen for the stent, the strut width in the low stress areas of the cylindrical element can be increased to enhance the radiopacity of the stent. However, if a high radiopaque material such as tantalum or platinum is used, it may be preferable to decrease the width of the strut in these low stress regions to decrease the overall radiopacity of the stent, if necessary. In this manner, rather than manufacturing a stent having wider strut widths in the low stress regions, as depicted in FIGS. 5–9, the stent would have strut widths that are narrower than the strut width in the high stress regions.

Figure 10:
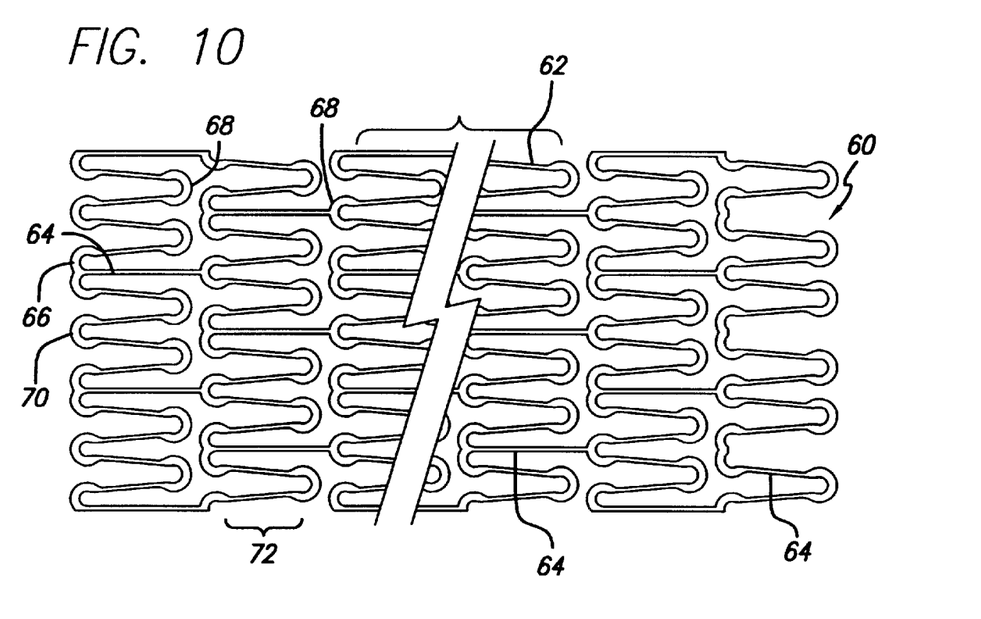
FIG. 10 is a plan view of one particular embodiment of a flattened stent of the present invention which illustrates the serpentine pattern including peaks and valleys which form the cylindrical elements of the stent and includes regions having narrower struts in the low stress regions.
Figure 11:
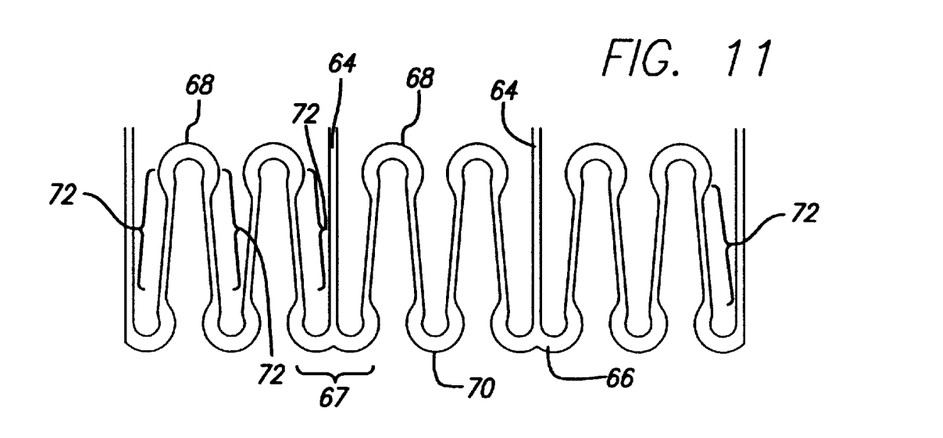
FIG. 11 is an enlarged partial view of the stent of FIG. 10 depicting one serpentine pattern along with the peaks and valleys which form one particular embodiment of a cylindrical element of a stent made in accordance with the present invention.

Referring now to FIGS. 10 and 11, a stent having strut widths in the low stress region which are narrower than the strut width in the high stress regions is shown. In this particular embodiment, the stent 60 includes cylindrical elements 62 which include peaks and valleys having U, Y, W and inverted U-shapes, in repeating patterns to form each individual cylindrical element 62. Each cylindrical element 62 is likewise connected to an adjacent cylindrical element via an interconnecting member 64. The high stress region of this stent 60 includes the double-curved portion (W) 66 located in the region of the valley 67 where each interconnecting member 64 is connected to an adjacent cylindrical element. The peak portion (inverted U) 68 and valley portion (U) 70 are also high stress regions of the stent. Again, during radial expansion, these high stress regions experience high stresses and strains which can cause cracks to form in the stent if the width of the strut is too large. In the design of this particular stent, the linking portions 72 which extend from peak portion to valley portion have a strut width that is narrower than the strut within the high stress regions. Additionally, the interconnecting member 64 also can be designed with a narrower strut as well. This particular stent design is particularly useful if a high radiopaque material, such as tantalum or platinum, is utilized to manufacture the stent since the narrower strut width in the low stress regions reduces the overall amount of stent material which would otherwise be visible during visualization when utilizing a fluoroscope or similar imaging equipment. Thus, the degree of radiopaqueness of the stent can be controlled. Of course, the strut width in these low stress regions cannot be designed too narrow, since a strut which is too narrow may effect the overall strength of the stent and the stent's ability to hold open the particular body lumen.

In the embodiment of FIGS. 7–9, each interconnecting member 43 and 53 is aligned collinearly with each other to form a continuous spine which extends along the length of the stent. This continuous spine 56 helps prevent the stent from shortening longitudinally when the cylindrical elements 42, 51 and 55 are expanded radially. These spines are advantageous especially when the stent is made from a self-expanding material. The number of spines 56 formed by the collinear arrangement of interconnecting elements can vary from one to as many as can be reasonably placed on a stent, however, for a minimal energy storage, two to four spines are recommended.

In many of the drawing figures, the present invention stent is depicted flat, in a plan view for ease of illustration. All of the embodiments depicted herein are cylindrically-shaped stents that are generally formed from tubing by laser cutting as described below.

One important feature of all of the embodiments of the present invention is the capability of the stents to expand from a low-profile diameter to a larger diameter, while still maintaining structural integrity in the expanded state and remaining highly flexible. Due to the novel structures, the stents of the present invention each have an overall expansion ratio of about 1.0 up to about 4.0 times the original diameter, or more, using certain compositions of stainless steel. For example, a 316L stainless steel stent of the invention can be radially expanded from a diameter of 1.0 unit up to a diameter of about 4.0 units, which deforms the structural members beyond the elastic limit. The stents still retain structural integrity in the expanded state and will serve to hold open the vessel in which they are implanted. Materials other than stainless steel (316L) may afford higher or lower expansion ratios without sacrificing structural integrity.

The stents of the present invention can be made in many ways. However, the preferred method of making the stent is to cut a thin-walled tubular member, such as stainless steel tubing to remove portions of the tubing in the desired pattern for the stent, leaving relatively untouched the portions of the metallic tubing which are to form the stent. It is preferred to cut the tubing in the desired pattern by means of a machine-controlled laser.

The tubing may be made of suitable biocompatible material such as stainless steel. The stainless steel tube may be alloy-type: 316L SS, Special Chemistry per ASTM F138-92 or ASTM F139-92 grade 2. Special Chemistry of type 316L per ASTM F138-92 or ASTM F139-92 Stainless Steel for Surgical Implants in weight percent.

| | |
|---|---|
| Carbon (C) | 0.03% max. |
| Manganese (Mn) | 2.00% max. |
| Phosphorous (P) | .025% max. |
| Sulphur (S) | 0.010% max. |
| Silicon (Si) | 0.75% max. |
| Chromium (Cr) | 17.00–19.00% |
| Nickel (Ni) | 13.00–15.50% |
| Molybdenum (Mo) | 2.00–3.00% |
| Nitrogen (N) | 0.10% max. |
| Copper (Cu) | 0.50% max. |
| Iron (Fe) | Balance |

The stent diameter is very small, so the tubing from which it is made must necessarily also have a small diameter. Typically the stent has an outer diameter on the order of about 0.06 inch in the unexpanded condition, the same outer diameter of the tubing from which it is made, and can be expanded to an outer diameter of 0.2 inch or more. The wall thickness of the tubing is about 0.003 inch.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished stent. Further details on how the tubing can be cut by a laser are found in U.S. Pat. Nos. 5,759,192 (Saunders) and 5,780,807 (Saunders), which have been assigned to Advanced Cardiovascular Systems, Inc. and are incorporated herein by reference in their entirety.

The process of cutting a pattern for the stent into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$, Nd or YAG laser set-up of the foregoing example. The program for control of the apparatus is dependent on the particular configuration used and the pattern to be ablated in the coding.

The stent of the present invention can be laser cut from a tube of super-elastic (sometimes called pseudo-elastic) nickel titanium (Nitinol) whose transformation temperature is below body temperature. A suitable composition of Nitinol used in the manufacture of a self-expanding stent of the present invention is approximately 55% nickel and 45% titanium (by weight) with trace amounts of other elements making up about 0.5% of the composition. The austenite transformation temperature is between about −15° C. and 0° C. in order to achieve superelastecity. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is approximately 0.5%. The breaking elongation is a minimum of 10%. It should be appreciated that other compositions of Nitinol can be utilized, as can other self-expanding alloys.

All of the stent diameters can be cut with the same stent pattern, and the stent is expanded and heat treated to be stable at the desired final diameter. The heat treatment also controls the transformation temperature of the Nitinol such that the stent is super elastic at body temperature. The transformation temperature is at or below body temperature so that the stent is superelastic at body temperature. The stent is electro polished to obtain a smooth finish with a thin layer of titanium oxide placed on the surface. The stent is usually implanted into the target vessel which is smaller than the stent diameter so that the stent applies a force to the vessel wall to keep it open.

The stent tubing of a self expanding stent made in accordance with the present invention may be made of suitable biocompatible material besides super-elastic nickel-titanium (NiTi) alloys. In this case the stent would be formed full size but deformed (e.g. compressed) to a smaller diameter onto the balloon of the delivery catheter to facilitate intra luminal delivery to a desired intra luminal site. For Nitinol, the stress induced by the deformation transforms the stent from an austenite phase to a martensite phase, and upon release of the force when the stent reaches the desired intra luminal location, allows the stent to expand due to the transformation back to the more stable austenite phase. Further details of how NiTi super-elastic alloys operate can be found in U.S. Pat. Nos. 4,665,906 (Jervis) and 5,067,957 (Jervis).

The stent diameters are very small, so the tubing from which it is made must necessarily also have a small diameter. For PTCA applications, typically the stent has an outer diameter on the order of about 1.65 mm (0.065 inches) in the unexpended condition, the same outer diameter of the hypo-tubing from which it is made, and can be expanded to an outer diameter of 5.08 mm (0.2 inches) or more. The wall thickness of the tubing is about 0.076 mm (0.003 inches). For stents implanted in other body lumens, such as PTA applications, the dimensions of the tubing are correspondingly larger. This stent is also designed for carotid applications, so the outer diameter of the tubing would typically be about 0.095 inches with a wall thickness of about 0.007 inches. The diameters of a carotid stent would be about 5–8mm. While it is preferred that the stents be made from laser cut tubing, those skilled in the art will realize that the stent can be laser cut from a flat sheet and then rolled up in a cylindrical configuration with the longitudinal edges welded to form a cylindrical member.

While the invention has been illustrated and described herein in terms of its use as intra vascular stents, it will be apparent to those skilled in the art that the stents can be used in other instances in all conduits in the body, such as, but not limited to, the urethra and esophagus. Since the stent of the present invention has the novel feature of self-expanding to a large diameter while retaining its structural integrity, it is particularly well suited for implantation in almost any vessel where such devices are used. This feature, coupled with limited longitudinal contraction of the stent when it is radially expanded, provide a highly desirable support member for all vessels in the body. Other modifications and improvements may be made without departing from the scope of the invention.

What is claimed is:

1. A longitudinally flexible stent for implanting in a body lumen and expandable from a contracted condition to an expanded condition, comprising:

a plurality of adjacent cylindrical elements defining struts, the cylindrical elements being substantially independently expandable in a radial direction, the plurality of cylindrical elements defining a first end and a second end with at least one cylindrical element forming a center section therebetween;

a plurality of interconnecting members extending between the adjacent cylindrical elements and connecting the adjacent cylindrical elements to one another, the interconnecting members connecting the end cylindrical elements to the center section having a taper with the wider portion of the taper being connected to the end cylindrical elements; and wherein at least one of said cylindrical elements has regions which experience high stresses and regions which experience low stresses during radial deployment, the width of the strut of the stent in the low stress regions being larger than the width of the strut of the stent in the high stress regions to increase the radiopacity of the stent.

2. The stent of claim 1, wherein each of said cylindrical elements has regions which experience high stresses and low stresses, the width of the struts in the low stress regions being larger than the width of the struts in the high stress regions to increase the radiopacity of the stent.

3. The stent of claim 1, wherein the cylindrical elements are formed in a generally serpentine wave pattern transverse to the longitudinal axis and contain alternating valley portions and, peak portions, which constitute the high stress regions of the stent.

4. The stent of claim 1, wherein the stent is made from a biocompatible material having low radiopacity.

5. The stent of claim 1, wherein the stent is formed from a biocompatible material selected from the group consisting of stainless steel, superelastic nickel titanium alloys, or thermal plastic polymers.

6. The stent of claim 1, wherein the width of the interconnecting members is larger than the width of the strut in the high stress regions.

7. The stent of claim 1, wherein each of the cylindrical elements at the first and second ends include at least three W-shaped portions.

8. A longitudinally flexible stent for implanting in a body lumen and expandable from a contracted condition to an expanded condition, comprising:

a plurality of adjacent cylindrical elements defining struts, each cylindrical element having a circumference extending about a longitudinal stent axis and being substantially independently expandable in a radial direction, wherein the plurality of adjacent cylindrical elements are arranged in alignment along the longitudinal stent axis and form a generally serpentine wave pattern transverse to the longitudinal axis containing alternating valley portions and peak portions with linking portions interconnecting said valley portions and peak portions, the plurality of cylindrical elements defining a first end and a second end with at least one cylindrical element forming a center section therebetween;

a plurality of interconnecting members extending between the adjacent cylindrical elements to connect adjacent cylindrical elements to one another, the interconnecting members connecting the end cylindrical elements to the center section having a taper with the wider portion of the taper being connected to the end cylindrical elements; and wherein at least one cylindrical element has linking portions having strut widths which are wider than the strut widths of the valley portions and peak portions of said cylindrical element.

9. The stent of claim 8, wherein each of said cylindrical elements has linking portions having strut widths which are wider than the strut widths of the valley portions and peak portion of said cylindrical element.

10. The stent of claim 8, wherein the stent is made from a biocompatible material having low radiopacity.

11. The stent of claim 8, wherein the stent is formed from a biocompatible material selected from the group consisting of stainless steel, superelastic nickel titanium alloys, or thermal plastic polymers.

12. The stent of claim 8, wherein the width of the interconnecting members is larger than the width of the strut in the valley portions and peak portions.

13. The stent of claim 8, wherein each of the cylindrical elements at the first and second ends includes a plurality of W-shaped portions having strut widths in the linking portion of the W-shaped portion which are larger than the strut width in the remaining portion of the W-shaped portion to increase the strength and radiopacity of the ends of the stent.

14. A method for constructing a longitudinally flexible stent for implanting in a body lumen which is expandable from a contracted condition to an expanded condition, the method comprising the steps of:

providing a plurality of adjacent cylindrical elements, each cylindrical element having a circumference extending about a longitudinal stent axis and being substantially independently expandable in a radial direction, the plurality of cylindrical elements defining a first end and a second end with at least one cylindrical element forming a center section therebetween;

forming struts in each cylindrical element in a generally serpentine wave pattern transverse to the longitudinal axis and containing alternating valley portions and peak portion with linking portions interconnecting each of said alternating valley portions and peak portions;

providing a plurality of interconnecting members extending between the adjacent cylindrical elements to connect adjacent cylindrical elements to one another, the interconnecting members connecting the end cylindrical elements to the center section having a taper with the wider portion of the taper being connected to the end cylindrical elements; and providing struts of the linking portions which are wider than the struts of the alternating valley portions and peak portions.

15. The method as defined in claim 14, wherein the stent is made from a biocompatible material having low radiopacity.

16. The method for constructing a longitudinally flexible stent as defined in claim 14, wherein interconnecting members have a strut width which is wider than the strut width of the alternating valley portions and peak portions.

* * * * *

UNITED STATES PATENT AND TRADEMARK OFFICE
CERTIFICATE OF CORRECTION

PATENT NO. : 6,540,774 B1
DATED : April 1, 2003
INVENTOR(S) : Daniel L. Cox

It is certified that error appears in the above-identified patent and that said Letters Patent is hereby corrected as shown below:

Title page,
Item [56], References Cited, U.S. PATENT DOCUMENTS, change "5,421,955  1/1998  Lau et al.", to read -- B1 5,421,995  1/1998  Lau et al. --.

Signed and Sealed this

Twenty-sixth Day of August, 2003

JAMES E. ROGAN
*Director of the United States Patent and Trademark Office*